United States Patent [19]
Cardin et al.

[11] Patent Number: 5,460,807
[45] Date of Patent: Oct. 24, 1995

[54] ANTIPROLIFERATIVE OLIGOMERS

[75] Inventors: Alan D. Cardin, Cincinnati; Steven J. Busch, West Chester, both of Ohio; Masayuki Mano, Izumo, Japan

[73] Assignee: Merrell Dow Pharmaceuticals Inc., Cincinnati, Ohio

[21] Appl. No.: 77,891

[22] Filed: Jun. 15, 1993

Related U.S. Application Data

[63] Continuation of Ser. No. 932,096, Aug. 19, 1992, abandoned.

[51] Int. Cl.$^6$ .................... A61K 31/785; A61K 31/795; C08G 71/02
[52] U.S. Cl. ................ 424/78.1; 424/78.11; 424/78.14; 424/78.08; 514/824; 514/825; 514/619; 514/626
[58] Field of Search .......................... 424/78.11, 78.14, 424/78.1; 514/824, 825, 619, 626

[56] References Cited

U.S. PATENT DOCUMENTS

| | | | |
|---|---|---|---|
| 2,833,744 | 5/1958 | Neher | 528/372 |
| 3,528,949 | 9/1970 | Rutledge | 528/367 |
| 3,993,625 | 11/1976 | Kurihara et al. | 521/63 |
| 4,073,768 | 2/1978 | Mark | 524/132 |
| 4,104,262 | 8/1978 | Schade | 528/295 |
| 4,312,855 | 1/1982 | Grand | 424/59 |
| 4,471,110 | 9/1984 | Christell | 528/337 |
| 4,604,404 | 8/1986 | Munson | 514/494 |
| 4,736,014 | 4/1988 | Engelhardt et al. | 528/295 |
| 4,756,907 | 7/1988 | Beck et al. | 424/496 |
| 4,824,916 | 4/1989 | Kershner et al. | 525/420 |
| 4,863,735 | 9/1989 | Kohn et al. | 424/422 |
| 4,895,660 | 1/1990 | Kershner et al. | 210/640 |
| 4,897,260 | 1/1990 | Ross et al. | 514/886 |
| 5,032,679 | 7/1991 | Brandley et al. | 536/21 |

FOREIGN PATENT DOCUMENTS

| | | |
|---|---|---|
| 0467185 | 1/1992 | European Pat. Off. . |
| 2307832 | 4/1976 | France . |
| 1067212 | 4/1968 | Germany . |
| 3345902 | 10/1990 | Germany . |
| 90094 | 10/1990 | South Africa . |
| 781479 | 8/1957 | United Kingdom . |
| 907829 | 10/1962 | United Kingdom . |
| 1393557 | 5/1975 | United Kingdom . |
| 9103226 | 3/1991 | WIPO . |
| 9200749 | 1/1992 | WIPO . |

OTHER PUBLICATIONS

Tyms et al., Cardin et al., J. Cell. Biochem. vol. SUPPL. pp. 365, 382 and 282 (1993).
A. W. Clowes et al., Nature, vol. 265, No. 5595, pp. 625–626 (1977).
A. L. Clowes et al., Journal of Vascular Surgery, vol. 10, No. 5, pp. 589–591 (1989).
E. J. Vandenberg et al., J. of Polymer Science, vol. 27, No. 11, pp. 3745–3757 (1989).
A. D. Cardin et al., Arteriosclerosis 9, pp. 21–32 (1989).
R. Montesano et al., Cell, vol. 42, 469–477 (1985).
R. M. Ottenbrite, ACS Symposium Series #186, pp. 205–220 (1982).
T. Kawasaki et al., J. Biochem 106, 401–405 (1989).
P. M. Rosoff et al., J. Med. Chem 263(36), 19535–19540 (1973).
R. Seiber et al., J. of Polymer Sci., Polymer Chem. Ed. 11(6), 1439–1442 (1973).
European Chem. News, p. 17 (Jul. 30, 1990).
C&E News, p. 11 (Jul. 16, 1990).
G. Odian, Principles of Polymerization, 2d, pp. 20–25 (1981).
R. K. Scopes, Protein Purification, pp. 186–198 (1987).
A. KoterA, Polymer Fractionation, pp. 43–65 (1967).
Polymer Fractionation, p. 462 (1967).
J. Chrom. Library, 41A, pp. A127–A208, A303–A399.
R. K. Scopes, Protein Purification, pp. 199–215 (1987).
DOWEX:ION Exchange, The Dow Chemical Co. 1958, pp. 39–66.
Macromolecules, vol. 1, Ch. 8 (1984).

Primary Examiner—Thurman K. Page
Assistant Examiner—Peter F. Kulkosky
Attorney, Agent, or Firm—Craig G. Svoboda; Steve Nesbitt

[57] ABSTRACT

The oligomers of the present invention are polyureas or polyamides having a number average molecular weight of <10,000. These oligomers are water-soluble, have a rigid backbone with a predictable anion spacing, and are pharmaceutically-acceptable. The oligomers are useful for inhibiting the proliferation of smooth muscle cell.

18 Claims, 5 Drawing Sheets

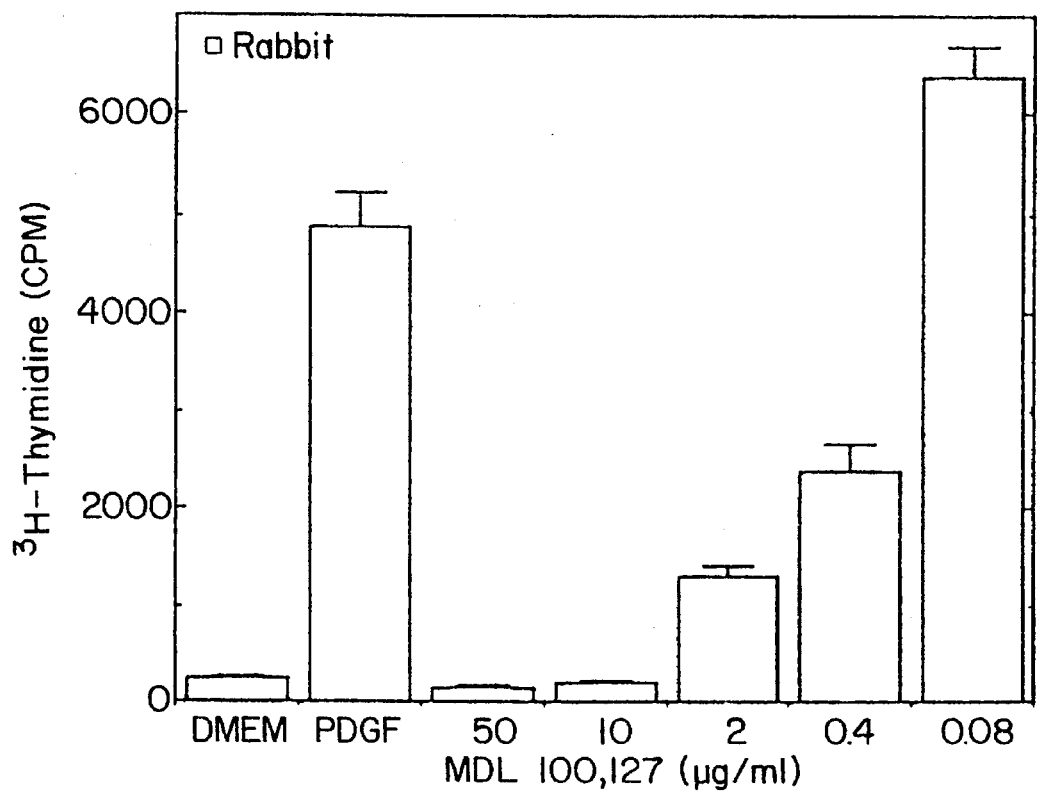
FIG. 4
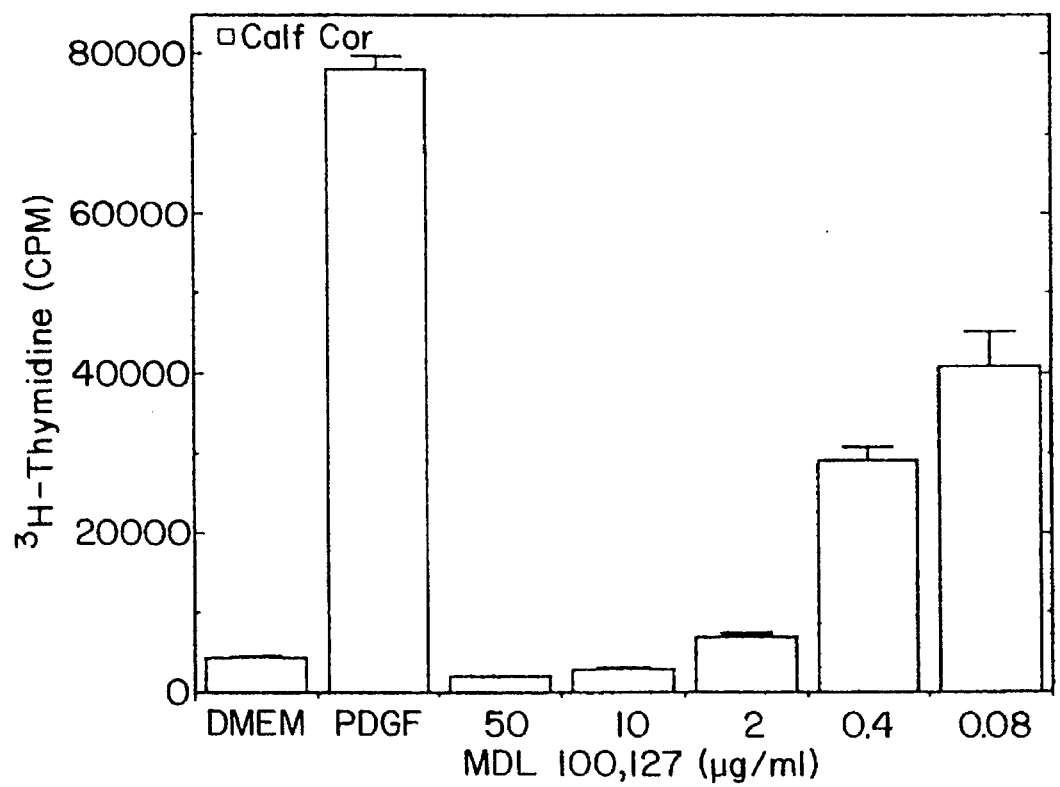

ANTIPROLIFERATIVE OLIGOMERS

This is a continuation of application Ser. No. 07/932,096, filed Aug. 19, 1992, now abandoned.

The invention relates to certain anionic oligomers which are useful antiproliferative agents by virtue of their ability to inhibit smooth muscle cell proliferation. These compounds can be used in the treatment of, for example, atherosclerosis.

Proliferation of smooth muscle cells in blood vessel walls occurs in reponse to vascular injury and in association with certain disease states. The proliferation of these cells can lead to the formation of pathologic lesions, for example, atherosclerosis and postsurgical vascular restenosis. Various glycosaminoglycans including heparin have been reported to inhibit smooth muscle cell proliferation. However, long term therapy with heparin is limited by its untoward side effects.

Applicants have discovered that a class of synthetic oligomers are heparinmimetic in that this class of oligomers inhibits smooth muscle cell proliferation in culture and in vivo. The synthetic oligomers do not possess the liabilities of prolonged heparin therapy. Such oligomers would thus be useful in the treatment of a variety of diseases and conditions associated with the smooth muscle cell and with other cells exhibiting unregulated cell proliferation.

SUMMARY OF THE INVENTION

This invention relates to the use of anionic polyamide and polyurea oligomers of formulae 1a and 1b, respectively, T,30 wherein X and $X^3$ each independently represent either a phenylene group of the formulae T,40 or a biphenylene group of the formula T,41 with the proviso that in a compound of formula 1a at least one of X and $X^3$ must be a biphenylene moiety;

X" is a group of the formulae T,50 m is an integer 0 or 1, with the proviso that in a compound of formula 1b when m is 0, R is a hydrogen atom;

X' can be selected from any of the phenyl or biphenyl groups of X and $X^3$;

n is an integer of from 3 to 50;

R represents a hydrogen atom, a $C_1$–$C_4$ alkyl group, a phenyl group, or a phenyl group optionally substituted with 1 or 2 substituents selected from —$SO_3R^2$, —$CO_2R_2$, —$PO_3(R^2)_2$, or —$OPO_3R^2$ and optionally substituted with from 1 to 3 substituents selected from chloro, bromo, or $C_1$–$C_4$ alkyl;

$R^1$ represents —$SO_3R^2$, —$CO_2R^2$, —$PO_3(R^2)_2$, or —$OPO_3R^2$;

$R^2$ represents a hydrogen atom or a pharmaceutically acceptable cation;

$R^3$ represents —R or —X"—$NH_2$, where R and X" are defined as before;

$R^6$ represents $H_2N$—X"—NH—, $R^2O$—, RNH—, or R—C(=O)—NH—X"—NH—; and $R^7$ represents a hydrogen atom, $R^2O$—C(=O)—X"—C(=O)—, R—C(=O)—, or RNH—C(=O)—X"—C(=O)—.

DETAILED DESCRIPTION OF THE INVENTION

The oligomers of the present invention are polyamides and polyureas having a number average molecular weight Mn of <10,000 comprising recurring units coupled by carbonyl linking moieties, said oligomer having anionic groups and predominantly linear geometry such that regular spacing between anionic groups exists in an aqueous medium. The oligomers are preferably linear in their backbone and also may be in their salt form. Particularly preferred salts are those that are pharmaceutically acceptable.

The term "pharmaceutically acceptable cation" means a cation acceptable for pharmaceutical use. Those cations that are not substantially toxic at the dosage administered to achieve the desired effect and do not independently possess significant pharmacological activity are included within the term "pharmaceutically acceptable cation". Illustratively, these salts include those of alkali metals, such as sodium and potassium; alkaline earth metals, such as calcium and magnesium; ammonium; light metals of Group IIIA including aluminum; and organic primary, secondary and tertiary amines, such as trialkylamines, including triethylamine, procaine, dibenzylaine, N,N'-dibenzylethylenediamine, dihydroabietylamine, N-($C_1$–$C_4$)alkylpiperidine, and any other suitable amine. Sodium and potassium salts are preferred. The term "pharmaceutically acceptable" means suitable for administration to warm blooded animals, especially human beings, and includes being nontoxic, e.g., suitable for pharmaceutical use and is not poisonous to the warm blooded animal. The pharmaceutically acceptable cations of the oligomers of the present invention are prepared by conventional ion exchange processes or by treating the $R^1$ acid with an appropriate base.

The oligomers of the present invention are low molecular weight, rigid backbone, water soluble polymers. Additionally, the oligomers have ordered anion spacing. By "ordered anion spacing" or "regular spacing between anionic groups" is meant that the anionic groups ($R^1$) are present in the backbone of the polymer at intervals determined by the starting material reagent used and the occurrence of the anionic groups is controlled in a predictable manner.

The terms "predominantly linear geometry" in an aqueous medium refers to the solution configuration of the oligomer. A method well known in the art for characterization of the solution configuration of polymer molecules is based on the following formula, referred to as the Mark-Houwink equation ["Introduction to Physical Polymer Science", ed. L. H. Sperling, pub. John Wiley & Sons (1985), pp. 81–83], $$[\eta]=KM^\alpha$$

wherein $\eta$ is intrinsic viscosity; M is weight average molecular weight; K is a constant related to chain bond dimension; and $\alpha$ is a constant determined by polymer configuration. The intrinsic viscosity (n) for a random coil polymer is $0.5<\alpha<0.9$; and for a linear polymer is $0.98<=\alpha<1.8$. This formula relates the solution viscosity "-" to the molecular weight "M". For this invention linear polymers are defined as having "$\alpha$" values greater than or equal to 0.9. For a rigid rod polymer the theoretical upper limit is 1.8. For a given molecular weight, a higher solution viscosity will be obtained from polymers with a linear configuration relative to those polymers which exist as a random coil. An additional consideration is that the "$\alpha$" value is a function of the solvent used. The "$\alpha$" for a given water soluble polymer may be different at different salt concentrations. For this invention, the salt concentration is set at the levels present in serum (approximately 80 g/L NaCl, 4 g/L KCl).

As used herein, the term "oligomer" encompasses all the possible values for n, e.g., 3 through 50. The oligomers are preferably linear with n equal to an integer from 3 to 50, preferably from 3 to 20, more preferably from 3 to 15. Of course, the n value is directly related to the molecular weight of the resulting oligomer. It is essential that these oligomers are of sufficiently low molecular weight in order to pass through the renal excretory membrane, but able to inhibit smooth muscle cell proliferation. The average molecular weight is governed by the stoichiometry of the reagents. The number average molecular weight (Mn) is <10,000, preferably from about 400 to about 10,000, and most preferably from about 1,000 to about 6,000.

For the purpose of the present invention, the oligomers described herein and physiologically acceptable salts thereof are considered equivalent. Physiologically acceptable salts refer to the salts of those bases which will form a salt with at least one acid group of the $R^1$ group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like.

As for all generic groups of chemical compounds having pharmacological and therapeutic activity, some compounds and subgroups of compounds are preferred. Of those compounds of formulae 1a and 1b, those compounds wherein n is an integer of from 3 to 18 are preferred, with the compounds wherein n is an integer of from 6 to 15 being more preferred, and those compounds wherein n is the integer 9 being most preferred. Also of the compounds of formulae 1a and 1b, those compounds wherein the $R^1$ groups are a —$SO_3R^2$, especially those wherein the $R^2$ group is a pharmaceutically acceptable cation, most especially those wherein the cation is a sodium cation, are preferred.

Also preferred are those polyamide compounds of formula 1a wherein $R^6$ is an R—C(=O)—NH—X"—NH— group, especially wherein R is an optionally substituted phenyl group, most especially those wherein R is a phenyl group or a 4-methylphenyl group and wherein X" is a group of one of the formula; T,100

$X^3$ is a phenylene group, especially a paraphenylene group of the formula; T,101

X is a biphenylene group, especially a biphenylene group of one of the formula and T,102

$R^7$ is an R—C(=O)— group especially wherein R is a phenyl group or a 4-methylphenyl group.

Also preferred are those polyurea compounds of formula 1b wherein

R is an optionally substituted phenyl group especially those wherein R is a phenyl group or a 4-methylphenyl group;

m is the integer 1;

X' is a phenyl or biphenyl group substituted by one or two —$SO_3R^2$ groups, especially those wherein $R^2$ is a sodium cation; and $R^3$ is an optionally substituted phenyl group especially those wherein R is a phenyl group or a 4-methylphenyl group.

Particularly preferred are those formula 1b compounds wherein X' is a phenyl or biphenyl group of one of the following formulae T,110 especially those wherein the $R^1$ group is a —$SO_3R^2$ wherein the $R^2$ group is a sodium cation.

The oligomers can be prepared by the procedures described in European Patent Application 91111315.7, filed Jul. 8, 1991, published Jan. 22, 1992.

The ability of the sulfonated oligomers of this invention to act as inhibitors of smooth muscle cell proliferation can be demonstrated by their ability to suppress DNA replication in cultured rat vascular smooth muscle cells (VSMC) stimulated to proliferate by the addition of serum (FIG. 1, Panel A) or instead, specific growth factors such as platelet derived growth factor (PDGF) or other agents (FIG. 2, Panels A and B, respectively) with known mitogenic activity on VSMC. The inhibitory activity is associated with polymer length being optimal at chain lengths between 3 and 15 and exhibits a dose-dependent inhibition of DNA replication and a corresponding decrease on cell numbers (FIG. 1, Panel B). The correlation between decreased DNA synthesis (FIG. 1, Panel A) and reduced cell numbers (FIG. 1, Panel B) in cultures after 72 hours of exposure to noncytotoxic concentrations of drug shows that these compounds are antiproliferative. In addition, the compounds block the proliferation of rabbit vascular smooth muscle cells (FIG. 3) and calf coronary (FIG. 4) and bovine pulmonary vascular smooth muscle cells (FIG. 5). They are also effective as antiproliferative agents when added as late as 12 hours post-mitogenic stimulation with the known smooth muscle cell mitogen PGDF (FIG. 6).

The bioavailability and in vivo activity of such compounds are demonstrated in FIG. 7. The experiment employs a rat restenosis model in which arterial denudation by balloon catheterization removes the arterial endothelial cell layer and stimulates VSMC migration and proliferation. A single intraperitoneal injection daily for two days of MDL 100,127 followed arterial denudation. The animals were then sacrificed and the DNA replication rate of the cells within the rat abdominal aorta was determined ex vivo. The aortas were removed from the animals, and pulsed as an explant with [$^3$H]thymidine (a DNA precursor) to measure its incorporation into DNA relative to that of aortas from the sham operated rats as negative controls, and with nontreated but balloon catheterized, animals as positive controls. The data of FIG. 7 show that MDL 100,127, when administered to rats, blocked DNA replication of the SMC in the aortic vessel wall of these animals.

The amount of the anionic polyamide and polyurea oligomer of formula 1a or 1b to be administered can vary widely according to the particular dosage unit employed, the period of treatment, the age and sex of the patient treated, the nature and extent of the disorder treated, and the particular anionic polyamide or polyurea of formulae 1a or 1b selected. Moreover the anionic polyamide and polyureas of formulae 1a and 1b can be used in conjunction with other agents useful in inhibiting smooth muscle cell proliferation and agents known to be useful to treat the symptoms of and complications associated with diseases and conditions caused by smooth muscle cell proliferation. The smooth muscle cell inhibitory effective amount of anionic polyamide and polyurea oligomer of formula 1a and 1b to be administered will generally range from about 15 mg/kg to 500 mg/kg. A unit dosage may contain from 25 to 500 mg of anionic polyamide and polyurea of formulae 1a and 1b, and can be taken one or more times per day. The polyamide and polyurea oligomers can be administered with a pharmaceutical carrier using conventional dosage unit forms either orally, parenterally, or topically.

The term "patient" used herein is taken to mean mammals such as primates, including humans, sheep, horses, cattle, pigs, dogs, cats, rats and mice.

The preferred route of administration is oral administration. For oral administration the anionic polyamide and polyurea oligomers can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The anionic polyamide and polyurea oligomers of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl- 1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the anionic polyamide and polyurea oligomers of formula 1a and 1b in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

DEFINITIONS

The terms used in the present application are defined as follows:

n represents the number average repeat length of the distribution through all formulae.

MDL 101,758, 100,127, and 101,044 mean poly{imino [2,2'-disulfo( 1,1'-biphenyl)-4,4'-diyl]iminocarbonyl}, alpha-{[(4-methylphenyl)amino] -carbonyl}-omega-[(4-methylphenyl)amino]- and is represented by Formula 1b above when R is 4-methylphenyl, $R^2$ is sodium, X is T,180 and n is 3, 6, and 9, respectively.

EXAMPLES

The following examples illustrate various aspects of the present invention: T,181

EXAMPLE 2

SMOOTH MUSCLE CELL PROLIFERATION ASSAYS

Cell Culture

Vascular smooth muscle cells (SMC) were isolated enzymatically from 2–3 thoracic aortas of male Sprague-Dawley rats (150 g). Briefly, aseptically obtained aortic strips were pre-digested at 37° C. in serum-free Dulbecco's Modified Eagle's Medium (DMEM) containing collagenase (1 mg/ml) and elastase (0.5 mg/ml) for 15–30 min. The luminal side of the aortic strip was gently scraped to remove the endothelium and the medial layer was separated from the adventitia. The medial layer was rinsed and digested for an additional 2 hours in fresh enzyme mixture at 37° C. Cells were grown in DMEM supplemented with 10% heat-inactivated fetal bovine serum (FBS), 2 mM L-glutamine, 100 units/ml penicillin, 100 mg/ml streptomycin, and 25 mM 4-(2-hydroxyethyl)-1-piperazineethane sulfonic acid (HEPES) at 37° C. with 5% $CO_2$ in humidified air. Subculture was performed every 7 days after the culture had reached confluence. Cultures between the 5th and 9th passages were employed in the present study.

3H-thymidine corporation

SMC were removed from their culture flasks by trypsinization and seeded at equal density ($5.0 \times 10^4$/well) into 24-well tissue culture plates. Cells were allowed to attach and grow to a near-confluent state in DMEM and 10% FBS (growth medium). This growth medium was then removed and replaced with DMEM and 0.2% FBS, and cells were incubated for 48–72 hours to achieve a growth arrest. Quiescent cells were then incubated for 21 h in DMEM and mitogens or growth factors (TDA, PDGF or FBS), containing various concentrations of compounds. In some experiments, quiescent cells were treated with various concentrations of compounds for 24 hours, washed twice with DPBS and incubated for 21 h in DMEM and growth factors. Finally, cells were incubated for 1–3 h in freshly prepared DMEM containing 1 μCI [3H-methyl]thymidine to measure DNA synthesis. Experiments were terminated by washing cells with ice cold PBS, precipitation of acid-insoluble material with ice-cold 10% trichloracetic acid (TCA) and extraction of DNA with 1N NaOH. After neutralization with 5N HCl, the contents of each well was added to a scintillation vial with scintillation cocktail and counted in a liquid scintillation counter.

Cell Growth

SMC were seeded into 12-well tissue culture plates at the density of $10^5$ cells/well. Cells were allowed to attach and grow for 3 days in growth medium. Medium was then replaced with fresh growth medium containing various concentrations of compounds (day 0) and incubated for 3 days. Cell numbers were counted on day 0 and day 3 in a Coulter counter.

Using these procedures, the effects of the oligomers of this invention on smooth muscle cell proliferation were determined and the results are indicated in FIGS. 1 through 7.

BRIEF DESCRIPTION OF THE DRAWINGS

FIG. 3 shows the inhibition of PDGF-induced proliferation of rabbit vascular smooth muscle cells by MDL 100,127. Numbers shown represent the [MDL 100,127] in μg/ml. Cells ($5 \times 10^4$) were serum-arrested in 0.2% FBS for 24 h, stimulated with PDGF in 0.2% horse plasma-derived serum (PDS) containing the indicated MDL 100,127 concentrations for 21 h and then pulse-labeled for 1 h with 1μCi $^3$H-thymidine/well. Total counts/well were determined after solubilization in 1M NaOH. DMEM: cells receiving DMEM only; PDGF: cells stimulated with 5 ng/m! PDGF; and cells stimulated with 5 ng/ml PDGF in 50, 10, 2,0.4 and 0.08 μg/ml MDL 100,127.

FIG. 4 shows the inhibition of PDGF-induced proliferation of calf coronary vsmc by MDL 100,127. Conditions and procedures are identical to those in FIG. 3.

Figure 1A:
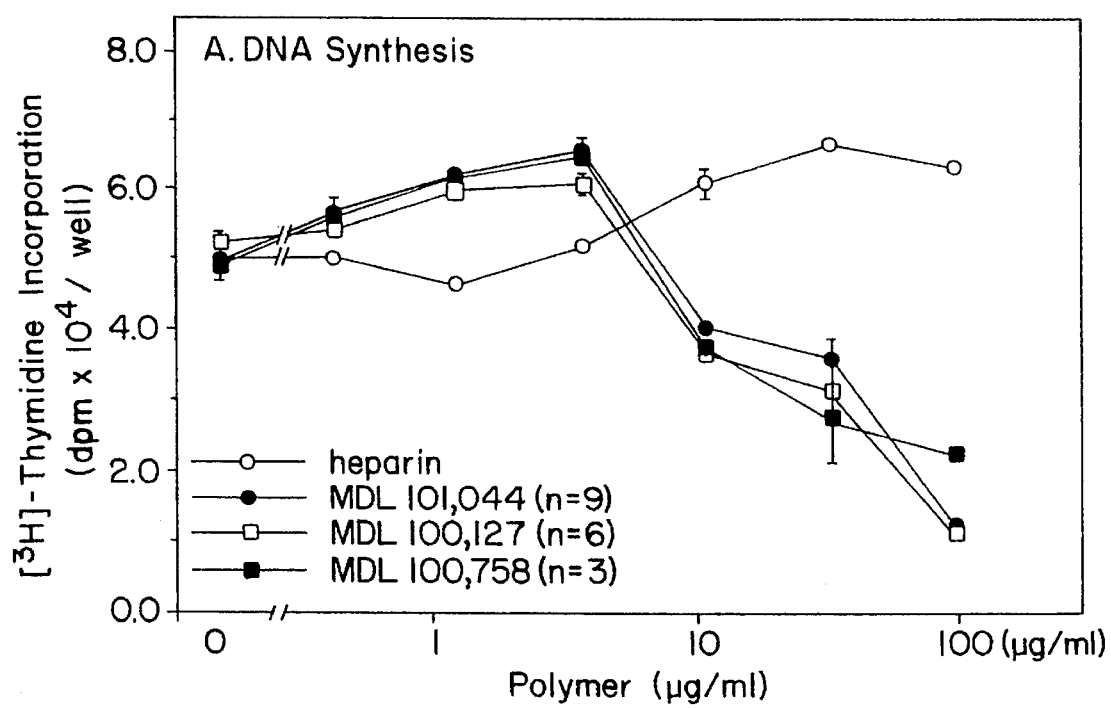
FIG. 1 shows the dose-dependent inhibition of serum-induced rat vsmc (rvsmc) proliferation by three polyamide biphenyl disulfonic acid phthalate copolymers, MDL 101,044 (n=9), 100,127 (n=6), and 100,758 (n=3). Panel A: Effect of compounds on DNA replication. $5 \times 10^4$ rvsmc were synchronized into the Go state by a 48 h preincubation in serum-deprived media containing 0.2% fetal bovine serum (FBS). Cells were then switched to Dulbecco's minimal essential media (DMEM) containing various concentrations of drug for 24 h. To stimulate proliferation FBS was added to a final concentration of 10% and the cells were incubated for 22 h. The medium was then replaced with DMEM containing 1 μCi of $^3$H-thymidine and pulse-labeled for 1 h. Cells were then washed 2 times with PBS, solubilized in 1M NaOH and counted. Panel B: Effect of compounds on cell numbers. Cells were seeded at $5.18 \times 10^4$ cells/well in DMEM +10% FBS containing various concentrations of compounds. Cells were incubated 3 days and then cell numbers counted. The results were normalized to cell cultures not receiving compound (control) and expressed as % of control. Viability was determined by trypan blue exclusion.
Figure 1B:
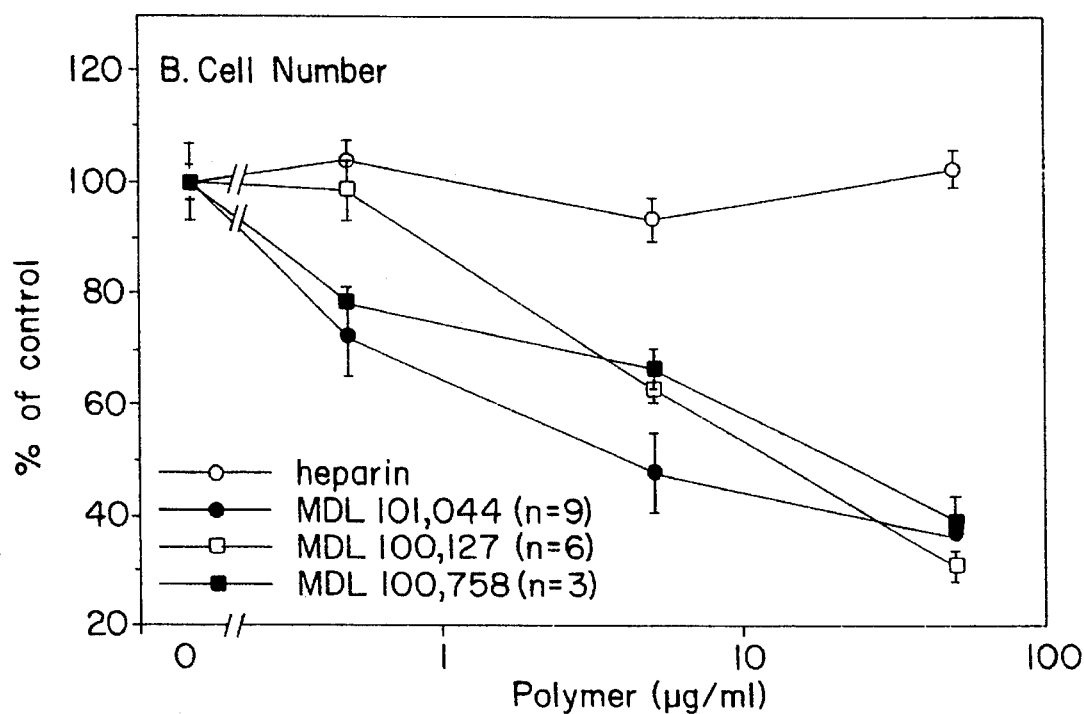
Figure 2A:
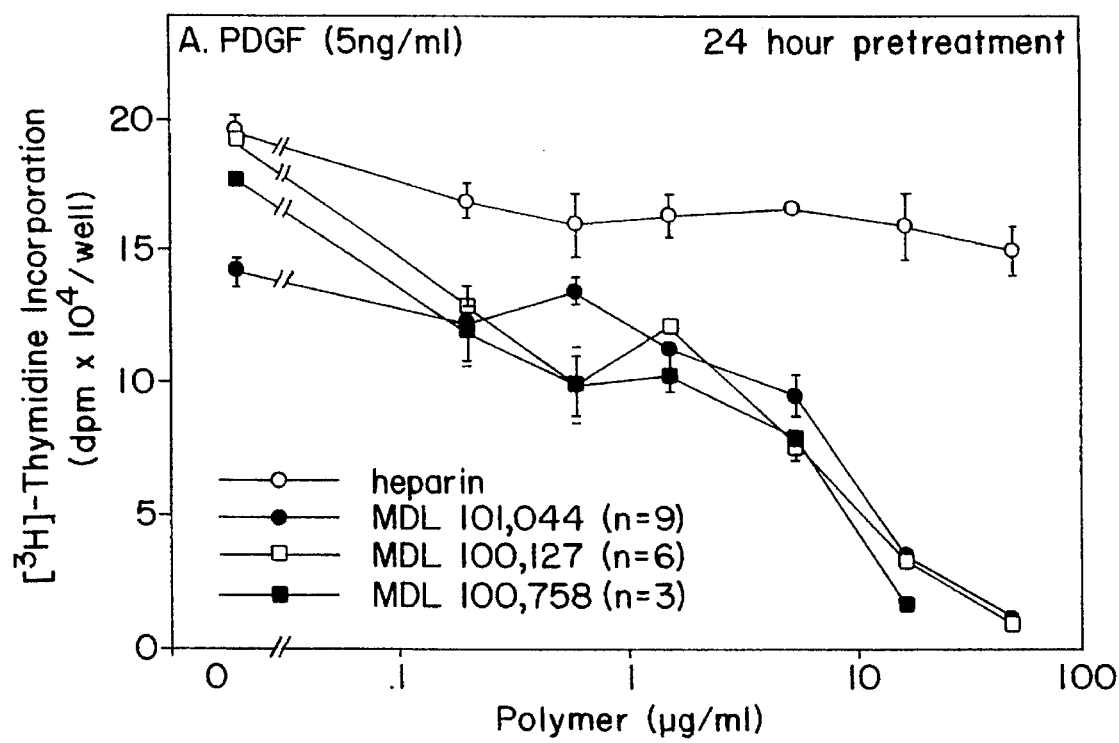
FIG. 2 Panel A shows the effect of the various polymers on PDGF-induced DNA replication as a measure of inhibition of rvsmc cell proliferation. Cells ($5 \times 10^4$) were growth-arrested in 0.2% FBS for 2 days to synchronize the cultures. Cells were washed twice with PBS and then treated with various concentrations of the indicated drugs in DMEM for 24 h. Cells were washed twice in PBS and then incubated in DMEM containing 1μCi/well $^3$H-thymidine. Proliferation was determined as in FIG. 1. Panel B: Effect of various polymers on phorbol ester (TPA)-induced rvsmc proliferation. Cells were seeded, treated with compounds and pulse-labeled with $^3$H-thymidine as performed in Panel A above.
Figure 2B:
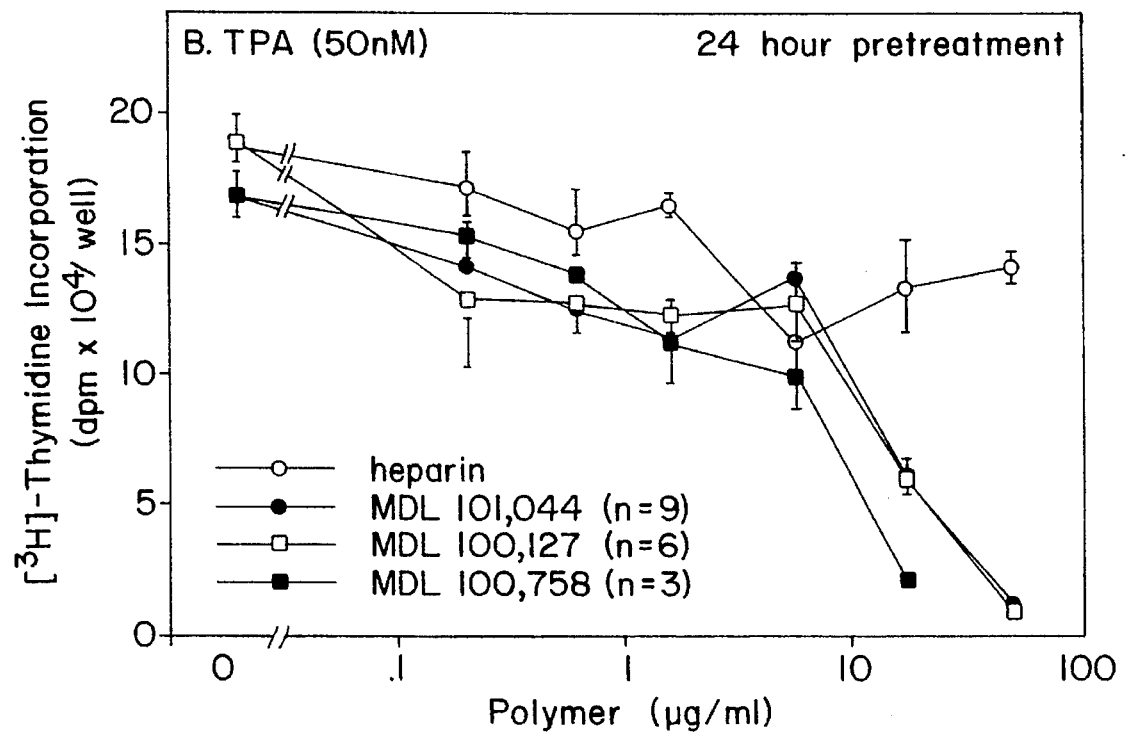
Figure 5:
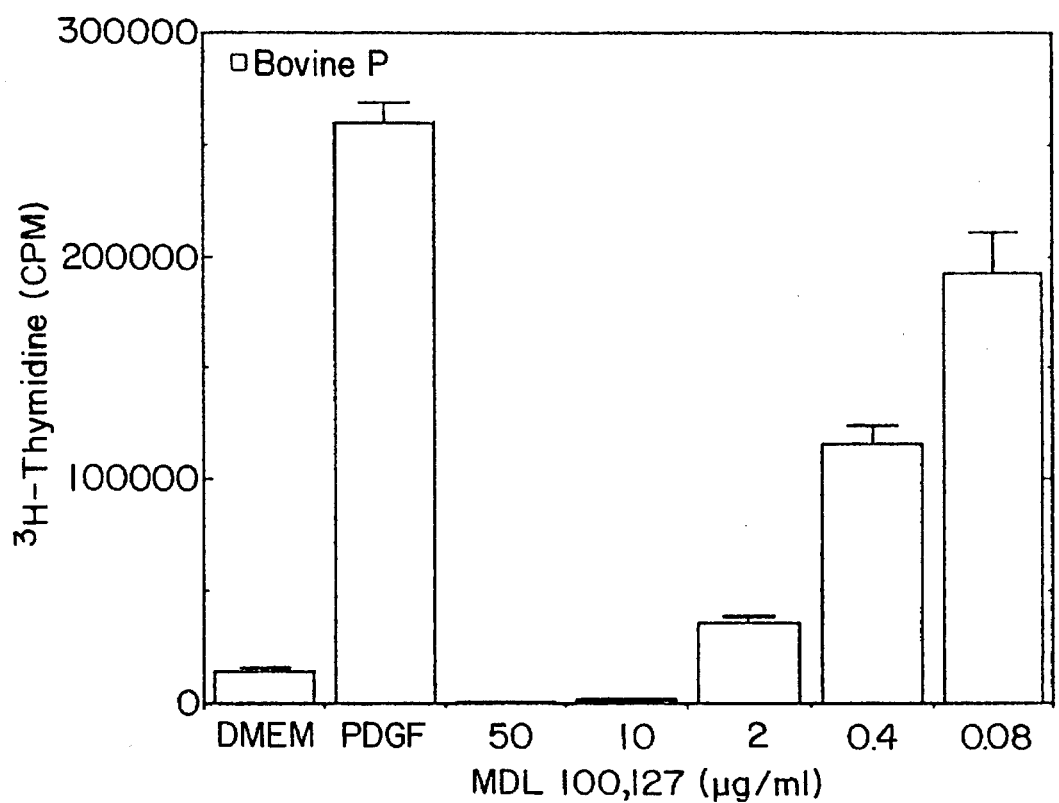
FIG. 5 shows the inhibition of PDGF-induced proliferation of calf pulmonary vascular smooth muscle cells by MDL 100,127. Conditions and procedures are identical to those of FIG. 3.
Figure 6:
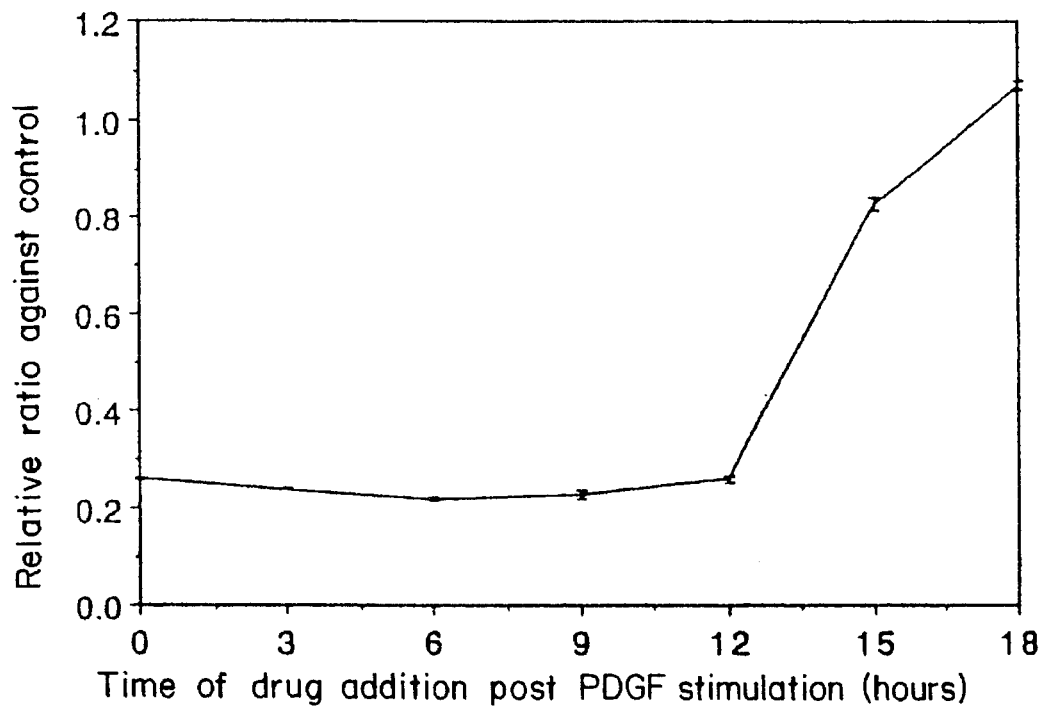
FIG. 6 shows the effect of 20 ug/ml MDL 100,127 on rvsmc proliferation when added at various times post-stimulation of cells with 5 ng/ml PDGF. Cells were synchronized for 48 h in 0.2% FBS and stimulated by 5 ng/ml PDGF in 0.2% PDS. MDL 100,127 was added either at the time of PDGF stimulation (time 0) or at various times post-stimulation with PDGF. Cultures were pulse-labeled for 2 h with 1 μCi 3H-thymidine/well beginning at 21 h post-stimulation with PDGF in all of the experiments performed. The cells were then harvested and counted. Parallel samples to which MDL 100,127 was added 15 h and 18 h post-PDGF stimulation were used to determine the amount of trichloroacetic acid (TCA) soluble and TCA insoluble counts present in total cellular soluble thymidine pools and DNA, respectively. The 15 h and 18 h samples were incubated for 6 and 3 h, respectively, in 20 µg/ml MDL 100,127 before the pulse label. The presence of these compounds did not block uptake of $^3$H-thymidine in soluble cellular pools or in DNA at these two time points. These findings show that once the rvsmc are committed to S-phase of the cell cycle the compounds do not block the uptake of thymidine. Thus, the antiproliferative block occurs prior to the commitment to S-phase and does not reflect a non-specific inhibition of uptake of thymidine by the compound.
Figure 7:
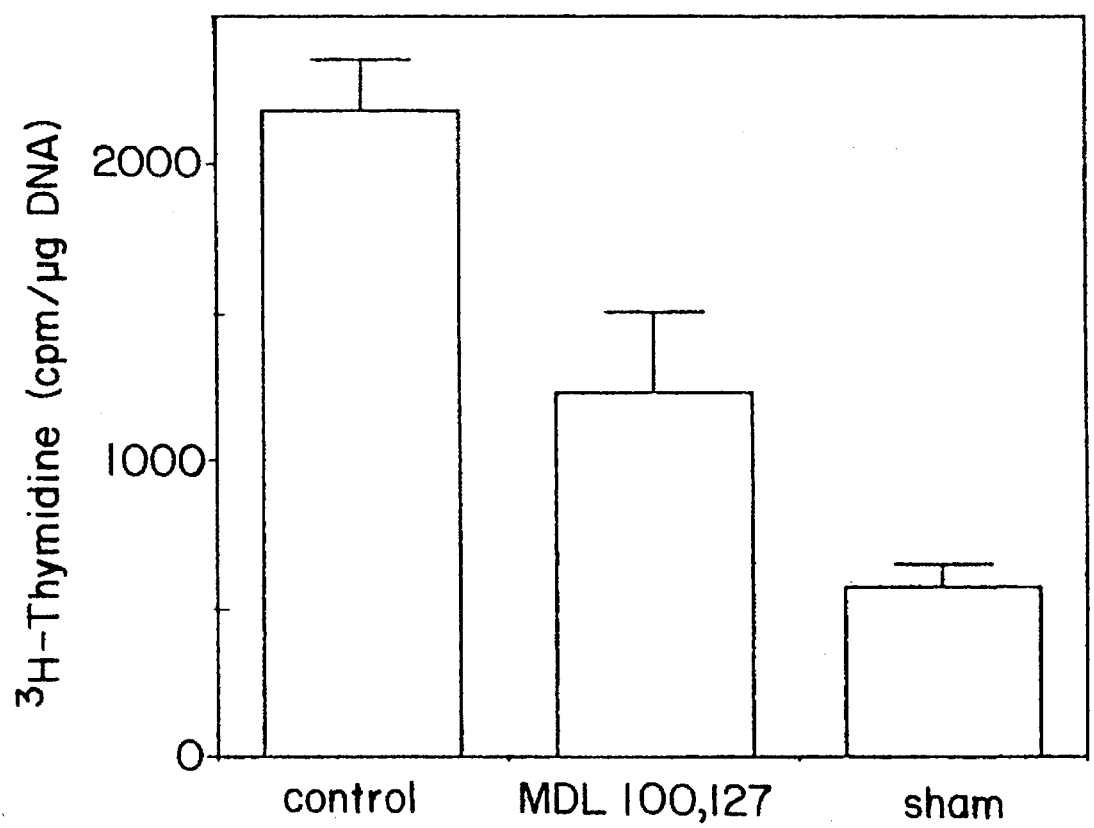
FIG. 7 shows that MDL 100,127 blocks the smooth muscle proliferative response in vivo in rats subjected to aortic balloon catheterization. The experimental protocol was a modification of the original aortic balloon injury model described by Baumgartner et al., *Ges. Exp. Med* 137, p. 227 (1963). Male Sprague-Dawley rats (160–190 g) were lightly anesthetized with 50 mg/kg, i.p. sodium thiamylol (Parke-Davis, Morris Pains, N.J.). A Fogarty embolectomy balloon (catheter size 2F, Baxter) was inserted by way of the carotid artery and passed down to the abdominal aorta. The catheter was withdrawn three times to induce injury with the balloon distended with 100% $CO_2$ (23 psi). The balloon was then deflated, the catheter removed, the animals sutured and allowed to recover. The positive control group (n=6) were balloon catheterized and did not receive drug. The experimental group (n=7) were also catheterized but received 30 mg/kg i.p. of MDL 100,127 at the time of balloon injury and at 24 h post-injury. The negative control group (n=6) were sham operated and did not receive drug. These animals received surgery and were treated indentically to the positive control group; they were not balloon catheterized. All animals survived the procedure and were sacrificed 48 h post-injury. Aortas were removed, adipose tissue was removed, the aortas explanted into DMEM containing 10 µCi $^3$H-thymidine and pulse-labeled for 1 hour. The tissues were then washed 2 times in PBS, the DNA extracted by standard procedures and counted. All animals receiving balloon catheterization showed visible signs of aortic injury of swelling and clot formation.

As is shown in FIG. 7, administration of MDL 100,127 significantly suppressed aortic smooth muscle cell proliferation as evidenced by the inhibition of $^3$H-thymidine into DNA relative to the positive control group (p<0.01). Slightly higher counts were obtained in the treated group relative to the sham operated group (p<0.05).

Table 1 shows that MDL 101,044 and 100,127 have minimal effects on the coagulation of bovine plasma relative to the potent anticoagulant heparin. The prothrombin (PT) and activated partial thromboplastin times (APTT) in seconds were only mildly elevated at the highest compound concentrations. T,240

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of inhibiting proliferation of smooth muscle cells in a patient in need thereof which comprises administering to the patient an antiproliferative amount of an anionic polyamide or polyurea oligomer of formulae 1a and 1b, respectively, T,330 wherein X and $X^3$ each independently represent either a phenylene group of the formulae: T,340 or a biphenylene group of the formulae: T,341 with the proviso that in a compound of formula 1a at least one of X and $X^3$ must be a biphenylene moiety;

X" is a group of the formulae: T,350 m is an integer 0 or 1, with the proviso that in a compound of formula 1b when m is 0, R is a hydrogen atom;

X' can be selected from any of the phenyl or biphenyl groups of X and $X^3$;

n is an integer of from 3 to 20;

R represents a hydrogen atom, a $C_1$–$C_4$ alkyl group, a phenyl group, or a phenyl group optionally substituted with 1 or 2 substituents selected from —$SO_3R^2$, —$CO_2R^2$, —$PO_3(R^2)_2$, or —$OPO_3R^2$ and optionally substituted with from 1 to 3 substituents selected from chloro, bromo, or $C_1$–$C_4$ alkyl;

$R^1$ represents —$SO_3R^2$, —$CO_2R^2$, —$PO_3(R^2)_2$, or —$OPO_3R^2$;

$R^2$ represents a hydrogen atom or a pharmaceutically acceptable cation;

$R^3$ represents —R or —X"—$NH_2$, where R and X" are defined as before;

$R^6$ represents $H_2N$—X"—NH—, $R_2O$—, RNH—, or R—C(=O)—NH—X"—NH—; and $R^7$ represents a hydrogen atom, $R^2O$—C(=O)—X"—C(=O)—, R—C(=O)—, or RNH—C(=O)—X"—C(=O)—.

2. A method of claim 1 wherein n is an integer of from 6 to 15.

3. A method of claim 1 wherein n is the integer 9.

4. A method of claim 2 wherein $R^1$ is a —$SO_3R^2$ group.

5. A method of claim 4 wherein $R^2$ is a sodium cation.

6. A method of claim 4 wherein $R^6$ is a R—C(=O)—NH—X"—NH— group.

7. A method of claim 6 wherein R is a phenyl or a 4-methylphenyl group.

8. A method of claim 6 wherein X" is a group of the formulae T,280

9. A method of claim 4 wherein $R^7$ is a R—C(=O)— group.

10. A method of claim 9 wherein R is a phenyl or a 4-methylphenyl group.

11. A method of claim 4 wherein $X^3$ is a paraphenylene group.

12. A method of claim 4 wherein X is a group of the formula T,281

13. A method of claim 4 wherein $R^6$ is a R—C(=O)—NH—X"—NH—, $X^3$ is a paraphenylene group, X is a biphenylene group of the formulae T,290 $R^7$ is a R—C(=O)— group, and R is a 4-methylphenyl group.

14. A method of claim 4 wherein m is the integer 1.

15. A method of claim 14 wherein R is a phenyl or 4-methylphenyl group.

16. A method of claim 14 wherein X' is a group of one of the formulae T,291

17. A method of claim 14 wherein R is a 4-methylphenyl group, X' is a group of the formulae T,292 and $R^3$ is a 4-methylphenyl group.

18. A method of claim 1 wherein the oligomer is a polyurea of Formula I wherein R and $R^3$ are a 4-methylphenyl group; m is 1; n is 3 to 15; X represents T,300 and $R^2$ is as defined as in claim 1.

* * * * *

UNITED STATES PATENT AND TRADEMARK OFFICE
CERTIFICATE OF CORRECTION

PATENT NO. : 5,460,807    Page 1 of 9

DATED : October 24, 1995

INVENTOR(S) : Alan D. Cardin, et al.

It is certified that error appears in the above-identified patent and that said Letters Patent is hereby corrected as shown below:

At column 1, line 29, the reference "T,30" should read:

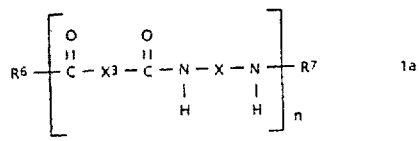

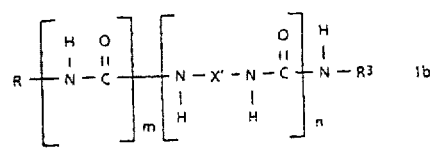

At column 1, line 32, the reference "T,40" should read:

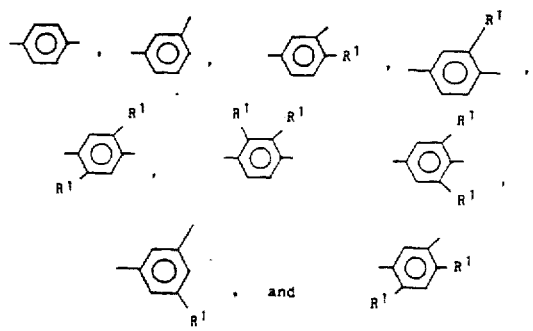

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

It is certified that error appears in the above-identified patent and that said Letters Patent is hereby corrected as shown below:

At column 1, line 33, the reference "T,41" should read:

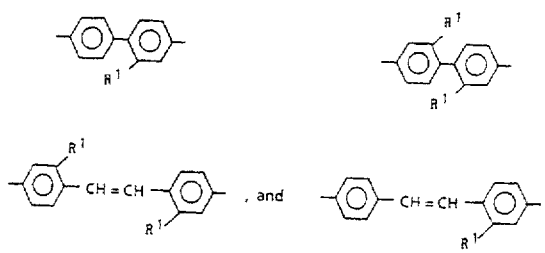

At column 1, line 36, the reference "T,50" should read:

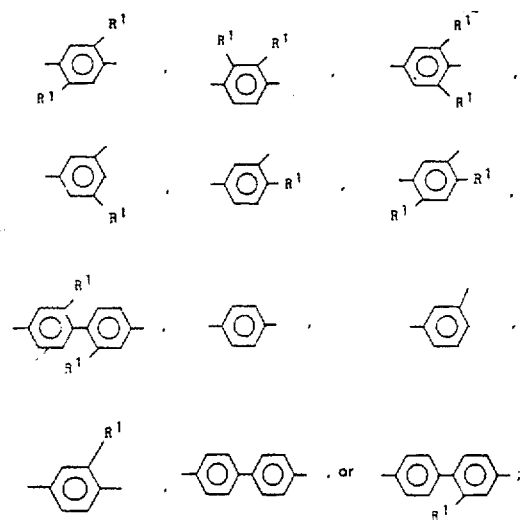

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

It is certified that error appears in the above-identified patent and that said Letters Patent is hereby corrected as shown below:

At column 3, line 40 the reference "T,100" should read:

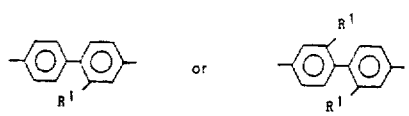

At column 3, line 42 the reference "T,101" should read:

At column 3, line 62, the reference "T,102" should read:

UNITED STATES PATENT AND TRADEMARK OFFICE
CERTIFICATE OF CORRECTION

PATENT NO. : 5,460,807

DATED : October 24, 1995

INVENTOR(S) :
Alan D. Cardin, et al.

It is certified that error appears in the above-identified patent and that said Letters Patent is hereby corrected as shown below:

At column 6, line 61, the reference "T,110" should read:

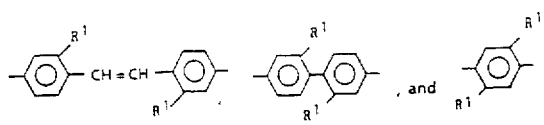

At column 6, line 67, the reference "T,181" should read:

Example 1

TAB. INHIBITION OF VASCULAR SMOOTH MUSCLE CELL
PROLIFERATION BY POLYMERS

| Stimulus | Treatment† | $IC_{50}$ (µg)ml | | |
|---|---|---|---|---|
| | | MDL 101,044 (n=9) | MDL 100,127 (N=6) | MDL 100,758 (n=3) |
| PDGF (5ng/ml) | post (24 hours) | 1.10 | 1.08 | 2.39 |
| | pre (24 hours) | 1.23 | 0.27 | 0.46 |
| TPA (50nM) | pre (24 hours) | 2.27 | 2.44 | 3.12 |
| FBS (10%) | post (24 hours) | >28.4 | >40.7 | >68.8 |
| | pre (24 hours) + post (21 hours) | 9.64 | 10.60 | 17.90 |

† post: length of incubation time with compound after VSMC stimulation;
pre: length of incubation time with compound prior to VSMC stimulation.

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

It is certified that error appears in the above-identified patent and that said Letters Patent is hereby corrected as shown below:

At column 9, line 53, the reference "T,240" should read:

TABLE 1
EFFECT OF COMPOUNDS ON THE COAGULATION PROPERTIES OF BOVINE PLASMA

| [Compound] µg/ml | Heparin | | MDL 101,044c | |
|---|---|---|---|---|
| | APTTa | PTa | APTT | PT |
| | 94 | 20 | 94 (92) | 20 (20) |
| 3.3 | 161 | 24 | 90 (92) | 20 (20) |
| 10.0 | NCDb | 58 | 91 (88) | 21 (21) |
| 16.7 | NCD | 91 | 97 (90) | 22 (21) |
| 23.3 | NCD | NCD | 120 (102) | 23 (22) |
| 30.0 | NCD | NCD | NCD (109) | 25 (23) | a APTT/PT, activated partial thromboplastin/prothrombin times measured in seconds
b NCD, no clot detected
c numbers in parenthesis represent MDL 100,127 (n-6)

At column 9, Claim 1, line 65, the reference "T,330" should read:

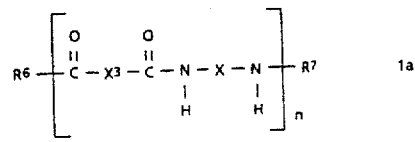

1a

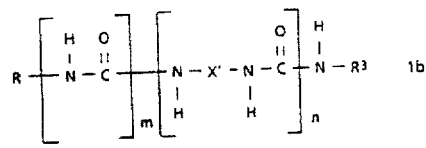

1b

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

Page 6 of 9

It is certified that error appears in the above-identified patent and that said Letters Patent is hereby corrected as shown below:

At column 10, Claim 1, line 1, the reference "T,340" should read:

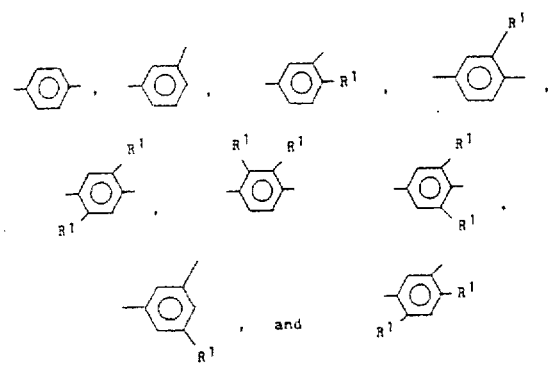

At column 10, Claim 1, line 2, the reference "T,341" should read:

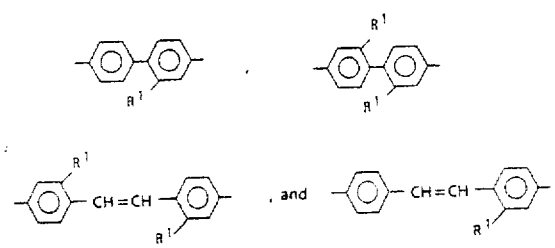

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

It is certified that error appears in the above-identified patent and that said Letters Patent is hereby corrected as shown below:

At column 10, Claim 1, line 5, the reference "T,350" should read:

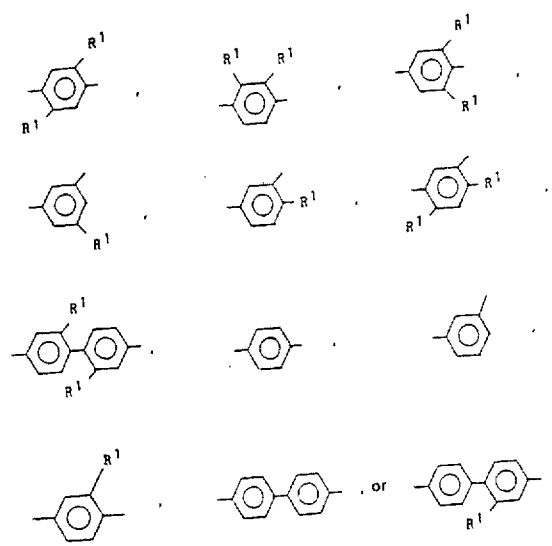

At column 10, Claim 8, line 40, the reference "T,280" should read:

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

It is certified that error appears in the above-identified patent and that said Letters Patent is hereby corrected as shown below:

At column 10, Claim 12, line 48, the reference "T,281" should read:

At column 10, Claim 13, line 51, the reference "T,290" should read:

At column 10, Claim 16, line 58, the reference "T,291" should read:

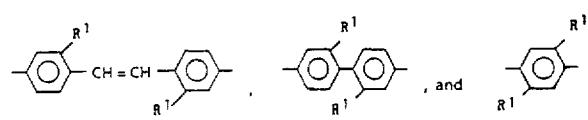

At column 10, Claim 17, line 60, the reference "T,292" should read:

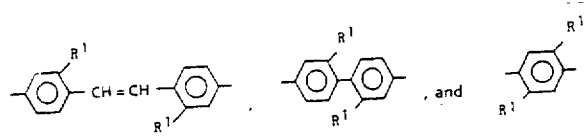

UNITED STATES PATENT AND TRADEMARK OFFICE
CERTIFICATE OF CORRECTION

PATENT NO. : 5,460,807

DATED : October 24, 1995

INVENTOR(S) : Alan D. Cardin, et al.

It is certified that error appears in the above-identified patent and that said Letters Patent is hereby corrected as shown below:

At column 10, Claim 18, line 64, the reference "T,300" should read:

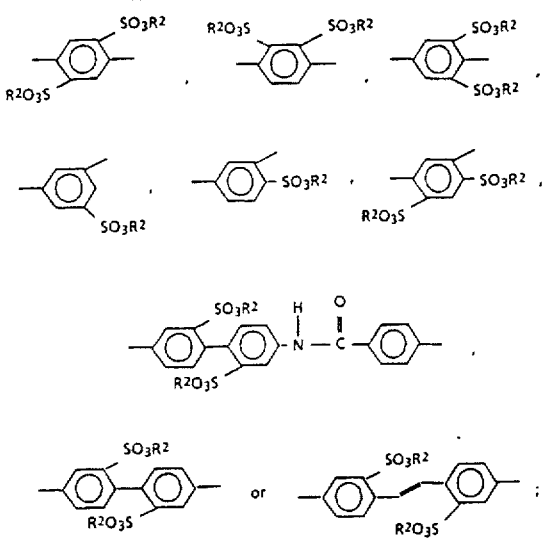

Signed and Sealed this

Fourth Day of May, 1999

Attest:

Q. TODD DICKINSON

Attesting Officer      Acting Commissioner of Patents and Trademarks